US00PP12402P2

(12) United States Plant Patent
Hansen

(10) Patent No.: US PP12,402 P2
(45) Date of Patent: Feb. 12, 2002

(54) HOSTA PLANT NAMED 'TITANIC'

(75) Inventor: Hans A. Hansen, Waseca, MN (US)

(73) Assignee: Shady Oaks Nursery, LLC, Waseca, MN (US)

( * ) Notice: Subject to any disclaimer, the term of this patent is extended or adjusted under 35 U.S.C. 154(b) by 0 days.

(21) Appl. No.: 09/454,948

(22) Filed: Dec. 3, 1999

(51) Int. Cl.[7] ..... A01H 5/00

(52) U.S. Cl. ..... Plt./353

(58) Field of Search ..... Plt./353

*Primary Examiner*—Bruce R. Campell
*Assistant Examiner*—Michelle Kizilkaya
(74) *Attorney, Agent, or Firm*—Vidas, Arrett & Steinkraus, P.A.

(57) ABSTRACT

A distinct cultivar of Hosta plant named 'Titanic', characterized by a unique variegation pattern with dark-green centers and relatively wide uneven yellow margins.

1 Drawing Sheet

BACKGROUND OF THE INVENTION

The present invention relates to a new and distinct cultivar of Hosta plant, botanically known as Hosta×'Titanic'.

The new cultivar was discovered by the inventor in Waseca, Minn., United States of America, as a naturally-occurring leaf mutation of the non-patented Hosta×'Sum and Substance', and was observed in a group of plants of the parent cultivar in 1995.

Asexual propagation of the new cultivar in 1999 at Waseca, Minn., The United States of America, by division and tissue culture has shown that the unique features of this new Hosta plant are stable and reproduced true to type in successive generations of asexual propagation.

BRIEF SUMMARY OF THE INVENTION

The following traits have been repeatedly observed and are determined to be the unique characteristics of Hosta× 'Titanic'. These characteristics in combination distinguish the new Hosta as a new and unique cultivar:

1. Large size cordate leaves with a heavy substance comprising a large sized plant mound; and 2. Dark green leaves with a wide, irregular yellow margin.

The new Hosta can be compared to its parent cultivar, 'Sum and Substance' but should also be compared to the cultivar known as 'Lady Isobel Barnett' (unpatented) which like the new Hosta disclosed herein is also a mutation of the Hosta 'Sum and Substance'. The new Hosta differs from 'Sum and Substance'. Hosta 'Sum and Substance' has a substantially uniform golden yellow color, whereas new Hosta has a variegation pattern characterized by leaves with green centers and yellow margins. Hosta×'Lady Isobel Barnett' also has a variegation pattern with a green center and a yellow margin, but the margin of the new Hosta is substantially wider than that of the 'Lady Isobel Barnett'.

The new Hosta cultivar has not been observed under all possible environmental conditions. The phenotype may vary to some extent with variations in environmental conditions such as temperature and light intensity, without any variance in genotype.

BRIEF DESCRIPTION OF THE PHOTOGRAPHS

The accompanying colored-photographs illustrate the overall appearance of the new cultivar, showing the colors as true as is reasonably possible to obtain in colored reproductions of this type.

The first photograph comprises a top perspective view of a typical plant of the new Hosta.

The second photograph comprises a close-up view of a typical leaf of the new Hosta.

Leaf colors in the photographs may appear differently from the actual colors due to light reflectance.

DETAILED DESCRIPTION OF THE INVENTION

In the following description, color references are made to The Royal Horticulture Society Colour Chart except where general terms of ordinary dictionary significance are used. The following observations and measurements describe four-year old plants, as depicted in the accompanying color photographs, which were grown outdoors in Waseca, Minn., United States of America.

Botanical classification: Hosta×'Titanic'.
Parentage: Hosta×'Sum and Substance'.
Propagation:
- *Method.*—By division and tissue culture.

Plant description:
- *Plant shape.*—Dome-shaped, symmetrical.
- *Growth habit.*—Initially upright when young, with leaves outwardly arching as they mature.
- *Culture.*—Light to medium shade in moist soil.
- *Plant type.*—Herbaceous perennial.
- *Plant height.*—About 16 inches from soil level to top of leaf plane.
- *Plant diameter.*—About 41 inches.
- *Vigor and growth rate.*—Moderate.
- *Disease resistance.*—No known particular resistance or susceptibility to disease. heavy leaf substance provides above average resistance to slug damage.

Foliage description:
- *Leaf shape.*—Broadly cordate with noticeably impressed veins.

*Leaf margin.*—Entire. Leaf texture: leaves are fairly smooth with heavy substance. Ridges are formed by the leaf veins, leaf surface is slightly shiny on top, glaucous bloom on under surface of leaf. Leaf size: Length: About 13 inches. Width: About 12 inches. Venation pattern: Campylodrome with 13–14 pairs of veins. Leaf color: Centers: dark green (about 139B) with an uneven wide leaf margin. Margins: yellow (about 151D), margins being ½ of an inch to 1 inches wide at base, the margin broadening at the widest point of the leaf where the margin is approximately 3 inches wide. The margin then narrows to a hairline width at the leaf tip.

Petioles description: In a mature plant petioles may have a length of approximately 25–30 centimeters in and a diameter of about 1 cm. Petiole color is substantially the same as the leaf interior.

Flower description:

*Flower shape.*—Funnel-shaped.

*Fragrance.*—No observed fragrance.

*Flower color.*—Pale Lavender 69D.

*Flower arrangement.*—Raceme comprised of numerous single flowers comprised of six tepals. Each inflorescence having around 25 to 30 flowers, with each flower lasting approximately 1 day.

*Flower size.*—Approximately 6–7 cm.

Scape description:

*Number.*—The number of scapes per plant is dependent on the maturity of the plant. Each mature eye comprising the clump may produce a flower scape under normal growing conditions. The scape has a color approximately the same as that the leaf interior. The length of the scape may be bewtween 30 to 45 inches long in a mature plant with a diameter of about 0.5 to 1 cm and having a round shape and smooth texture. The scapes will droop in full flower from the weight of the flowers.

Description of reproductive organs: The reproductive organs comprise six stamens and a compound ovary having three locules. The size of the anther is Approximately 0.5 cm with a color of 11A. The pollen is average in abundance and is color 11A. The stigma is a three lobed stigma of color 155C, and the style has a color of 155A and is approximately 5 to 6 cm in length.

Seed development: Has not been observed.

Root development: From transfer to rooting media in tissue culture, rooting takes approximately 4 weeks at about 68 degrees Fahrenheit. After transfer from stage III in tissue culture to planting into soil in a green house, a wel l rooted plant is produced in approximately 8 weeks with a day time temperature of about 68 degrees Fahrenheit (about 65 degrees Fahrenheit at night) and a soil temperature of about 78 degrees Fahrenheit.

I claim:

1. A new and distinct cultivar of Hosta plant named 'Titanic', as illustrated and described.

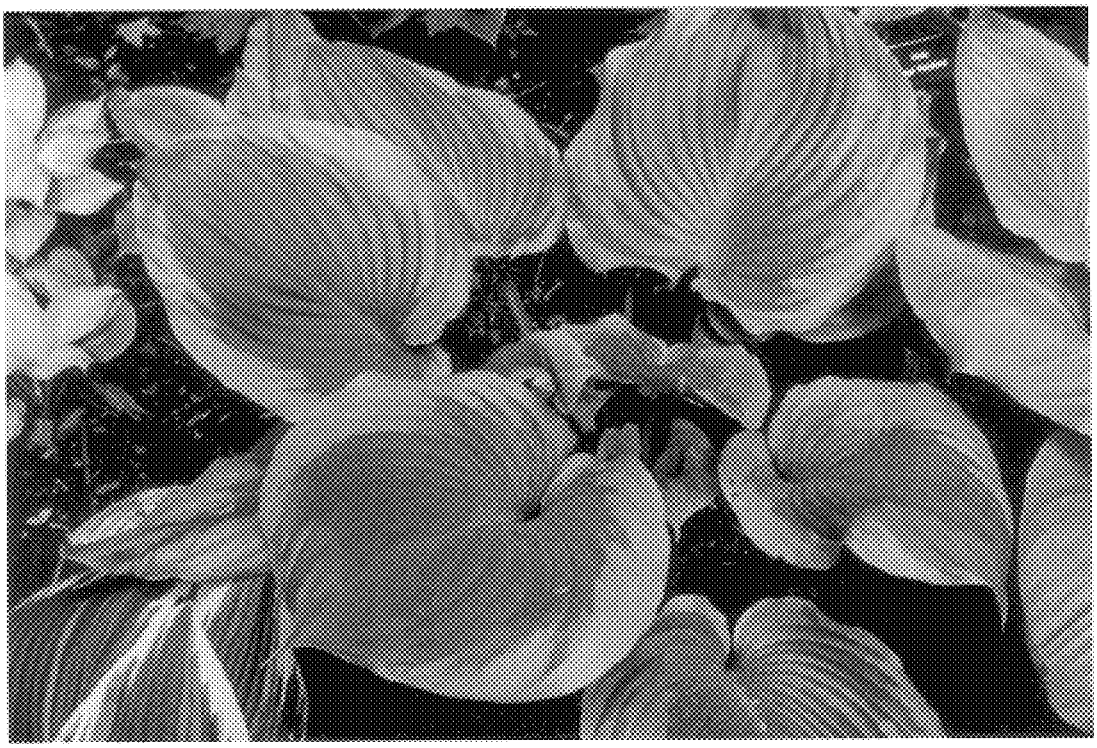
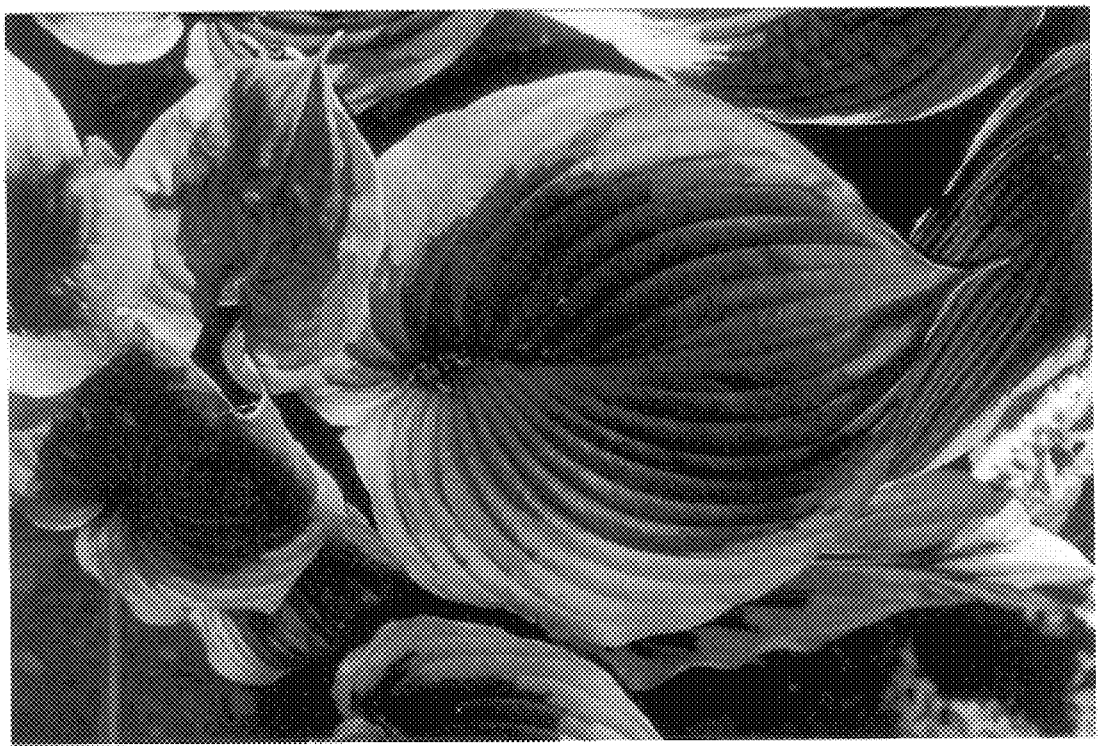

* * * * *